(12) United States Patent
Birkbeck

(10) Patent No.: US 10,934,240 B2
(45) Date of Patent: Mar. 2, 2021

(54) CYCLOHEXENE DERIVATIVES AS PERFUMING INGREDIENTS

(71) Applicant: Firmenich SA, Satigny (CH)

(72) Inventor: Anthony Alexander Birkbeck, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/492,778

(22) PCT Filed: Mar. 15, 2018

(86) PCT No.: PCT/EP2018/056498
§ 371 (c)(1),
(2) Date: Sep. 10, 2019

(87) PCT Pub. No.: WO2018/167200
PCT Pub. Date: Sep. 20, 2018

(65) Prior Publication Data
US 2020/0071253 A1 Mar. 5, 2020

(30) Foreign Application Priority Data
Mar. 15, 2017 (EP) .................................. 17161067

(51) Int. Cl.
*A61K 8/18* (2006.01)
*A61Q 13/00* (2006.01)
*A61K 8/00* (2006.01)
*C07C 47/225* (2006.01)
*C11B 9/00* (2006.01)

(52) U.S. Cl.
CPC ........ *C07C 47/225* (2013.01); *C07C 2601/16* (2017.05); *C11B 9/0034* (2013.01)

(58) Field of Classification Search
CPC .. C07C 47/225; C07C 260/116; C11B 9/0034
USPC .................................................. 512/22, 8, 1
See application file for complete search history.

(56) References Cited

U.S. PATENT DOCUMENTS

| | | | |
|---|---|---|---|
| 4,396,670 A | 8/1983 | Sinclair | |
| 2005/0101498 A1* | 5/2005 | Marty | C07C 47/225 510/106 |
| 2013/0090390 A1 | 4/2013 | Singer et al. | |

FOREIGN PATENT DOCUMENTS

| EP | 1054053 A2 | 11/2000 |
|---|---|---|
| WO | 0141915 A1 | 6/2001 |

OTHER PUBLICATIONS

International Search Report and Written Opinion received in International Patent Application No. PCT/EP2018/056498, dated May 8, 2018, 12 pages.
Bône et al., "Microencapsulated Fragrances in Melamine Formaldehyde Resins", CHIMIA, 2011, vol. 65, No. 3, pp. 177-181.
Dietrich et al., "Amino resin microcapsules", Acta Polymerica,1989, vol. 40, No. 4, pp. 243-251.
Dietrich et al., "Amino resin microcapsules", Acta Polymerica, 1990, vol. 41, No. 2, pp. 91-95.
Lee et al., "Microencapsulation of fragrant oil via in situ polymerization: effects of pH and melamineformaldehyde molar ratio", Journal of Microencapsulation: Micro and Nano Carriers, 2002, vol. 19, No. 5, pp. 559-569.

\* cited by examiner

*Primary Examiner* — Jessica Whiteley
(74) *Attorney, Agent, or Firm* — Armstrong Teasdale LLP

(57) ABSTRACT

The present invention concerns a compound of formula (I) in the form of any one of its stereoisomers or a mixture thereof, and wherein n is 0 or 1; R and R', independently from each other, represent a hydrogen atom or a $C_{1-2}$ linear alkyl group provided that one of said groups represents a hydrogen atom and the other a $C_{1-2}$ linear alkyl group; each $R^1$, independently from each other, represents a hydrogen atom or a methyl group; and $R^2$ and $R^3$ represent, independently of each other, a $C_{1-3}$ linear alkyl group; or $R^2$ and $R^3$, when taken together, represent a $C_{4-5}$ linear, branched alkanediyl or alkenediyl. The use of compound of formula (I) as perfuming ingredients of floral type and the invention's compounds as part of a perfuming composition or of a perfuming consumer product are also part of the present invention.

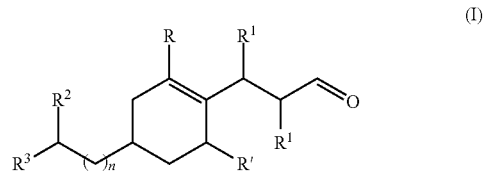

(I)

17 Claims, No Drawings

CYCLOHEXENE DERIVATIVES AS PERFUMING INGREDIENTS

CROSS-REFERENCE TO RELATED APPLICATIONS

This application is a U.S. National Phase Application of PCT/EP2018/056498, filed Mar. 15, 2018, which claims the benefit of priority to European Patent Application No. 17161067.8, filed Mar. 15, 2017, the entire contents of which are hereby incorporated by reference herein.

TECHNICAL FIELD

The present invention relates to the field of perfumery. More particularly, it concerns the use as perfuming ingredient of compounds of formula (I) as defined below, which are useful perfuming ingredients of floral type. Therefore, following what is mentioned herein, the present invention comprises the invention's compounds as part of a perfuming composition or of a perfuming consumer product.

BACKGROUND

Some of the most sought ingredients in the perfumery field are the ones imparting a floral impression and in particular a lily of the valley odor, particularly because this delicate floral odor does not survive even the mildest of extraction methods to yield an essential oil. Said note is very appreciated and used in a multitude of perfumed consumer products. For many decades, a lot of effort has been invested in finding compounds possessing this very complex white floral odor, especially since the use of Lilial® (2-methyl-3-[4-(2-methyl-2-propanyl)phenyl]propanal, trademark from Givaudan-Roure SA, Vernier, Suisse) representing one of the most valuable perfuming ingredients with a lily of the valley and watery connotation, has been limited due to various reasons.

So, there is a need to develop novel perfuming ingredients conferring a floral odor note being as close as possible to the natural odor of the lily of the valley blossom.

US 2013/0090390 reports as a compound imparting said olfactive properties 3-(4-isopropylcylohex-1-en-1-yl)propanal. In particular, (R)-3-(4-isopropylcylohex-1-en-1-yl)propanal imparts a lily of the valley, floral, sweet, watery, powdery and ozone-like note, whereas (S)-3-(4-isopropylcyclohex-1-en-1-yl)propanal is less preferred and confers a lily of the valley, fruity, green, watery and aldehydic-like note.

The present invention provides a novel perfumery ingredient imparting lily of the valley note, by using compounds of formula (I) which imparts a less aggressive odor than the prior art. The prior art document mentioned above does not report or suggest any organoleptic properties of the compounds of formula (I), or any use of said compounds in the field of perfumery.

SUMMARY OF THE INVENTION

The invention relates to compound of formula (I) which imparts an odor of floral type, in particular lily of the valley (also named muguet) which is much appreciated in perfumery.

So, a first object of the present invention is a compound of formula

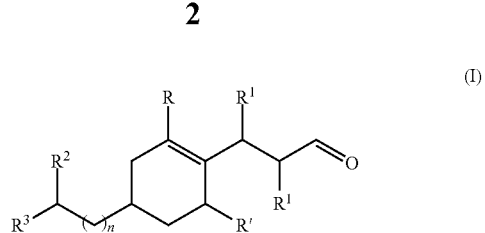

in the form of any one of its stereoisomers or a mixture thereof, and wherein n is 0 or 1; R and R', independently from each other, represent a hydrogen atom or a $C_{1-2}$ linear alkyl group provided that one of said groups represents a hydrogen atom and the other a $C_{1-2}$ linear alkyl group; each $R^1$, independently from each other, represents a hydrogen atom or a methyl group; and $R^2$ and $R^3$ represent, independently of each other, a $C_{1-3}$ linear alkyl group; or $R^2$ and $R^3$, when taken together, represent a $C_{4-5}$ linear, branched alkanediyl or alkenediyl.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is the use as a perfuming ingredient of a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I) or a composition as defined above.

DESCRIPTION OF THE INVENTION

Surprisingly, it has now been discovered that compounds of formula (I) possess a very interesting odor note with a lily of the valley connotation which is particularly appreciated. A first object of the present invention is a compound of formula

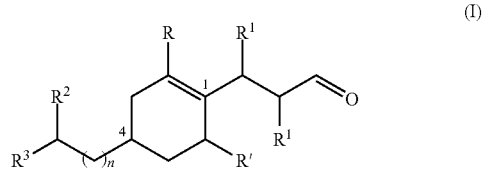

in the form of any one of its stereoisomers or a mixture thereof, and wherein n is 0 or 1; R and R', independently from each other, represent a hydrogen atom or a $C_{1-2}$ linear alkyl group provided that one of said groups represents a hydrogen atom and the other a $C_{1-2}$ linear alkyl group; each $R^1$, independently from each other, represents a hydrogen atom or a methyl group; and $R^2$ and $R^3$ represent, independently of each other, a $C_{1-3}$ linear alkyl group; or $R^2$ and $R^3$, when taken together, represent a $C_{4-5}$ linear or branched alkanediyl or alkenediyl. Said compounds can be used as perfuming ingredients, for instance to impart odor notes of the lily of the valley/cyclamen type with aldehydic/watery connotation.

According to any one of the above embodiments of the invention, said compounds (I) are $C_{13}$-$C_{19}$ compounds, preferably $C_{13}$-$C_{16}$ compounds.

For the sake of clarity, by the expression "any one of its stereoisomers or a mixture thereof", or the similar, it is meant the normal meaning understood by a person skilled in the art, i.e. that the invention's compound can be a pure enantiomer (if compound possesses one stereocenter) or a pure diastereoisiomer (if compound possesses at least two stereocenters) or a mixture of enantiomers or diastereoisomers.

According to any one of the above embodiments of the invention, the compound of the present invention is of formula

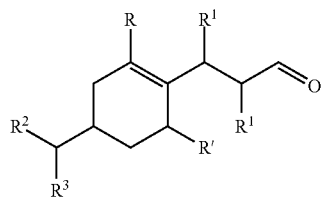

(II)

in the form of any one of its stereoisomers or a mixture thereof and wherein R, R', $R^1$, $R^2$ and $R^3$ have the same meaning as above.

According to any one of the above embodiments of the invention, the compound of the present invention is of formula

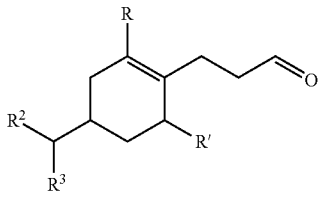

(III)

in the form of any one of its stereoisomers or a mixture thereof and wherein R, R', $R^2$ and $R^3$ have the same meaning as above.

According to any one of the above embodiments of the invention, n may be 0 or 1. Preferably n may be 0.

According to any one of the above embodiments of the invention, $R^1$ may be a hydrogen atom or a methyl group. Preferably, $R^1$ may be a hydrogen atom.

According to any one of the above embodiments of the invention, $R^2$ may be $C_{1-3}$ linear alkyl group. Preferably, $R^2$ may be a methyl or an ethyl group. Even more preferably, $R^2$ may be a methyl group.

According to any one of the above embodiments of the invention, $R^3$ may be a $C_{1-3}$ linear alkyl group. Preferably, $R^3$ may be a methyl or an ethyl group. Even more preferably, $R^3$ may be a methyl group.

According to any one of the above embodiments of the invention, $R^2$ and $R^3$, when taken together, may be a $C_{4-5}$ linear or branched alkanediyl or alkenediyl. Preferably, $R^2$ and $R^3$, when taken together, may be a $C_{4-5}$ linear or branched alkanediyl. Even more preferably, $R^2$ and $R^3$, when taken together, may be a $C_4$ linear alkanediyl.

According to any one of the above embodiments of the invention, R and R', independently from each other, represent a hydrogen atom or a $C_{1-2}$ linear alkyl group provided that one of said groups represents a hydrogen atom and the other a $C_{1-2}$ linear alkyl group. Preferably, R and R', independently from each other, represent a hydrogen atom or a methyl group provided that one of said groups represents a hydrogen atom and the other a methyl group.

According to a particular embodiment of the invention, R represents a hydrogen atom and R' represents a methyl group. The R' group and the group of carbon 4 could be cis, trans or mixtures thereof.

According to another particular embodiment of the invention, R represents a methyl group and R' represents a hydrogen atom.

According to a particular embodiment of the invention, compound of formula (I) is in the form of a mixture of regioisomers wherein, for one regioisomer, R represents a $C_{1-2}$ linear alkyl group, preferably a methyl group, and R' represents a hydrogen atom; and for the other regioisomer, R represents a hydrogen atom and R' represents a $C_{1-2}$ linear alkyl group, preferably a methyl group. Preferably the compound of formula (I) is a mixture of regioisomers wherein, for one regioisomer, R represents $C_{1-2}$ linear alkyl group, preferably a methyl group and R' represents a hydrogen atom; and for the other regioisomer R represents a hydrogen atom and R' represents a $C_{1-2}$ linear alkyl group, preferably a methyl group wherein the two regiosiomers are in a molar ratio ranging from 5:95 to 95:5, from 10:90 to 90:10, from 20:80 to 80:20, from 30:70 to 70:30, from 40:60 to 60:40. Preferably the compound of formula (I) is a mixture of regioisomers wherein, for one regioisomer, R represents $C_{1-2}$ linear alkyl group, preferably a methyl group and R' represents a hydrogen atom; and for the other regioisomer R represents a hydrogen atom and R' represents a $C_{1-2}$ linear alkyl group, preferably a methyl group wherein the two regiosiomers are in a molar ratio of about 5:95, 10:90, 20:80, 30:70, 40:60, 50:50, 60:40, 70:30, 80:20, 90:10 or 95:5. Preferably compound of formula (I) is in the form of a mixture of regioisomers containing at least 50% of regioisomer wherein R represents a methyl group and R' represents a hydrogen atom (e.g. 3-(4-isopropyl-2-methyl-1-cyclohexen-1-yl)propanal). Even more preferably, compound of formula (I) is in the form of a mixture of regioisomers containing at least 70% regioisomer wherein R represents a methyl group and R' represents a hydrogen atom (e.g. 3-(4-isopropyl-2-methyl-1-cyclohexen-1-yl)propanal). Even more preferably the compound of formula (I) is a mixture of 3-(4-isopropyl-6-methylcyclohex-1-en-1-yl)propanal and 3-(4-isopropyl-2-methylcyclohex-1-en-1-yl)propanal, preferably in a respective molar ratio of 25:75.

As specific examples of the invention's compounds, one may cite, as non-limiting example, a mixture comprising 3-(4-isopropyl-6-methyl-1-cyclohexen-1-yl)propanal in a form of cis and trans isomer (3:1) and 3-(4-isopropyl-2-methyl-1-cyclohexen-1-yl)propanal in a respective molar ratio of 25:75 which possesses an aldehydic, floral/lily of the valley note being fresh and clear (transparent) with orange and watery connotations. Said mixture is very powerful. In comparison, a mixture comprising 3-[6-methyl-4-(2-methyl-2-propanyl)-1-cyclohexen-1-yl]propanal and 3-[2-methyl-4-(2-methyl-2-propanyl)-1-cyclohexen-1-yl]propanal in a respective molar ratio of 26:74, while conferring also an aldehydic, floral/lily of the valley note, it distinguished from the invention's compound by a very poor performance; i.e.

the organoleptic impact is very weak and much less powerful than the above-mentioned mixture.

As other example, one may cite 3-(4-isopropyl-2-methyl-1-cyclohexen-1-yl)propanal, which possesses an odor similar to the one mentioned above.

According to a particular embodiment of the invention, the compounds of formula (I) are a mixture comprising cis-3-(4-isopropyl-6-methyl-1-cyclohexen-1-yl)propanal, trans-3-(4-isopropyl-6-methyl-1-cyclohexen-1-yl)propanal and 3-(4-isopropyl-2-methyl-1-cyclohexen-1-yl)propanal in a respective molar ratio of 6:19:75.

When the odor of the invention's compounds is compared with that of the prior art compound (R)-3-(4-isopropylcyclohex-1-en-1-yl)propanal, then the invention's compounds distinguish themselves by a clearly floral cyclamen/lily of the valley note allied with a texture fleshy and petal-like and by lacking the green-aldehydic/classic-aldehydic character of the prior art. The odor of the invention's compounds is also finer and devoid of the soapy/fatty side of aldehyde so characteristic of the prior art compound. The invention's compound is nicer than the prior art which confers a more technical aspect; i.e. detergent and clean aldehyde. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture threof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
Aldehydic ingredients: decanal, dodecanal, 2-methyl-undecanal, 10-undecenal, octanal and/or nonenal;
Aromatic-herbal ingredients: eucalyptus oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate , high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde,
amylcinnamic aldehyde, 4-phenyl-2-butanone, isononyle acetate, 4-(1,1-diméthyléthyl)-1-cyclohexyl acetate, verdyl isobutyrate and/or mixture of methylionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;
Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;
Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol -5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.01% to 1% by weight, or even more, of the invention's compounds relative to the total weight of the consumer product into which they are incorporated.

The invention's compounds can be prepared according to a method to a method as describes herein-below.

EXAMPLES

The invention will now be described in further detail by way of the following examples, wherein the abbreviations have the usual meaning in the art, the temperatures are indicated in degrees centigrade (° C.) ; NMR spectra were acquired using either a Bruker Advance II Ultrashield 400 plus operating at (400 MHz ($^1$H) and 100 MHz ($^{13}$C) or a Bruker Advance III 500 plus operating at (500 MHz ($^1$H) and 125 MHz ($^{13}$C) or a Bruker Advance III 600 cryoprobe operating at (600 MHz ($^1$H) and 150 MHz ($^{13}$C). Spectra were internally referenced and chemical shifts δ are indicated in ppm relative to TMS 0.0 ppm and coupling constants J are expressed in Hz.

Example 1

Synthesis of Compounds of Formula (I); i.e Mixture of 3-(4-isopropyl-6-methylcyclohex-1-en-1-yl) propanal and 3-(4-isopropyl-2-methylcyclohex-1-en-1-yl)propanal a) Preparation of 2-hydroxy-5-isopropylbenzaldehyde
Preparation following *Tet. Lett.*, 2005, 46, 3357.

A suspension of 4-isopropyl phenol (50 g, 367 mmol), MgCl$_2$ (69.9 g, 734 mmol), Et$_3$N (74.3 g, 734 mmol) and paraformaldehyde (34.4 g, 1.1 mol) in THF (250 mL) was heated under reflux for 6 hours then cooled. The reaction mixture was poured into MTBE (200 mL) then washed carefully with citric acid (5%), then NaHCO$_3$, the organic phase was then dried over Na$_2$SO$_4$ then filtered and the solvents removed in vacuo to yield the crude aldehyde, 70 g. Further purification by Fischer distillation, at a temperature between 93 and 100° C. at 3 mbar, gave the pure aldehyde, 45.4 g (75%).

$^1$H NMR (400 MHz, CDCl$_3$): δ 1.25 (d, J 6.5, 6H), 2.91 (m7, J 6.5, 1H),6.85 (s, 1H), 6.89 (dd, J 8, 1, 1H), 7.47 (d, J 8, 1H), 9.83, (s, 1H), 11.0 (s, 1H, OH) ppm;

$^{13}$C NMR (100 MHz, CDCl$_3$): δ 23.9 (q), 33.1 (d), 117.4 (d), 120.4 (s), 130.8 (d), 135.7 (d), 140.3 (s), 159.8 (s), 196.7 (d) ppm.

b) Preparation of 2-methyl 4 isopropyl phenol

In a s/s 150 mL autoclave a solution of the 2-hydroxy-5-isopropylbenzaldehyde (29.5 g, 179 mmol) in methanol (50 ml) containing pTSA (100 mg) and palladized charcoal (5%, 1.0 g) was evacuated under vacuum and purged with hydrogen gas 5 times then stirred under an atmosphere of hydrogen gas (25 bar) for 12 hours at ambient temperature. The suspension was filtered and washed with MTBE (2×100 mL) then the filtrate washed with NaHCO$_3$ solution dried and the solvents removed in vacuo to yield the crude phenol, 30 g. Further purification by bulb to bulb (Kugelrohr) distillation temp 120° C. vacuum 1 mbar gave the pure phenol, 26.5 g (84%).

$^1$H NMR (400 MHz, CDCl$_3$): δ 1.20 (d, J 6.7, 6H), 2.22 (s, 3H), 2.80 (m7, J 6.9, 1H), 4.93 (bs, 1H), 6.68 (d, J 7.9, 1H), 6.91 (dd, J 7.9, 1.4, 1H), 6.97 (d, J 1.4, 1H) ppm;

$^{13}$C NMR (100 MHz, CDCl$_3$): δ 15.9 (q), 24.2 (q), 33.3 (d), 114.7 (d), 123.5 (s), 124.8 (d), 129.0 (d), 141.2 (s), 151.6 (s) ppm.

c) Preparation of 4-isopropyl-2-methylcyclohexan-1-one

In a s/s 150 mL autoclave a suspension of the 2-methyl-4-isopropyl phenol (22.5 g, 174 mmol) water (4 g) and palladized charcoal (0.9 g) was evacuated under vacuum then purged with hydrogen gas 5 times, then stirred under an atmosphere of hydrogen gas (20 bar) at 120° C. for 24 hours. The reaction was cooled then filtered and washed with MTBE. The filtrate was concentrated in vacuo to yield the crude cyclohexanone containing cyclohexanols, 19.4 g. This mixture was dissolved in DCM (200 mL) then treated with PCC (27.0 g, 125 mmol) and silica (28 g) for 6 hours at ambient temperature. The suspension was diluted with MTBE then filtered through silica and washed with MTBE. The filtrate was concentrated in vacuo to yield the crude cyclohexanone 19.7 g. Further purification by bulb to bulb distillation (Kügelrohr, 5.0 mbar, 90-95° C.) gave the pure cyclohexanone, 18.2 gas a mixture of cis and trans isomers (5:1, 67%).

Cis Isomer $^1$H NMR (400 MHz, CDCl$_3$): δ 0.91 (d, J 6.7, 6H), 1.01 (d, J 6.5, 3H), 1.67 (t, J 12.5, 1H), 1.41 (qd, J 12.7, 5.1, 1H), 1.56 (m7, J 6.5, 1H), 1.59-1.75 (m, 3 H), 2.00-2.09 (m, 2H), 2.26-2.47 (m, 3H) ppm;

$^{13}$C NMR (100 MHz, CDCl$_3$): δ 16.4 (q), 20.4 (q), 20.4 (q), 29.1 (t), 29.9 (d), 36.4 (t), 37.7 (t), 38.2 (d), 42.3 (d), 215.4 (s) ppm.

Trans Isomer Characteristic Signals $^1$H NMR (400 MHz, CDCl$_3$): δ 0.94 (d, J 2.9, 3H), 0.96 (d, J 2.9, 3H), 1.11 (d, J 6.8, 3H) ppm.

$^{13}$C NMR (100 MHz, CDCl$_3$): δ 14.7 (q), 20.0 (q), 30.7 (t), 32.0 (d), 39.3 (t), 41.3 (t), 43.2 (d), 44.4 (d), 213.7 (s) ppm.

d) Preparation of 1-(2-(1,3-dioxolan-2-yl)ethyl)-4-isopropyl-2-methylcyclohexan-1-ol Under atmosphere of argon, to a suspension of magnesium turnings (2.81 g, 105 mmol) in THF (80 mL), a solution of 2-(2-bromoethyl)-1,3-dioxolane (20.0 g, 105 mmol) in THF (20 mL) was added slowly dropwise. The exotherm was maintained at 40° C. with a cooling bath. After a further 60 mins of stirring at ambient temperature, a solution of the 4-isopropyl-2-methylcyclohexan-1-one (16.2 g, 105 mmol) in THF (25 mL) was added. After a further 4 hours at ambient temperature, the reaction mixture was poured onto a mixture of ice and saturated ammonium chloride solution, extracted with MTBE twice, and the combined organic phase washed with saturated sodium bicarbonate solution then brine, dried over Na$_2$SO$_4$, filtered and the solvents removed in vacuo to yield the crude alcohol 35.0 g which was used directly in the next step without further purification.

e) Preparation of a Mixture of 3-(4-isopropyl-6-methylcyclohex-1-en-1-yl)propanal and 3-(4-isopropyl-2-methylcyclohex-1-en-1-yl)propanal The 1-(2-(1,3-dioxolan-2-yl)ethyl)-4-isopropyl-2-methylcyclohexan-1-ol (35.0 g, 137 mmol) was dissolved in pyridine (150 mL) and the solution cooled at 0° C. POCl$_3$ (31.5 g, 205 mmol) was added slowly dropwise. The solution was slowly warmed to ambient temperature then heated at 50° C. for 18 hours. The mixture was then cooled and poured cautiously into ice, then extracted with MTBE and the organic phase washed cautiously with saturated NaHCO$_3$ solution, then dilute sulfuric acid (5%, 2×), brine, dried over Na$_2$SO$_4$, filtered and the solvents removed in vacuo to yield the crude acetal, 12.9 g.

The crude acetal obtained previously (12.9 g, 54.1 mmol) was dissolved in a mixture of acetone (150 mL) and water (75 mL). Then HCl (conc. 2.5 mL) was added slowly and the solution heated under reflux for 4 hours then cooled. The solution was diluted with saturated NaHCO$_3$ solution then extracted with MTBE twice, the combined organic phase was washed with brine, then dried over Na$_2$SO$_4$, filtered and the solvents removed in vacuo to yield the crude aldehyde. Further purification by distillation (Kügelrohr, 1.0 mbar, 95-100° C.) gave the aldehyde 7.5 g. Further purification by chromatography (SiO$_2$) using heptane:EtOAc (99:1) gave the aldehyde as a mixture of isomers (trans 3-(4-isopropyl-6-methylcyclohex-1-en-1-yl)propanal; cis 3-(4-isopropyl-6-methylcyclohex-1-en-1-yl)propanal and 3-(4-isopropyl-2-methylcyclohex-1-en-1-yl)propanal in a respective ratio 6:18:76), which was redistilled as before to give the aldehyde, 4.9 g (6:19:75).

3-(4-isopropyl-2-methylcyclohex-1-en-1-yl)propanal $^1$H NMR (500 MHz, CDCl$_3$): δ 0.87 (d, J 2.6, 3H), 0.89 (d, J 2.6, 3H), 1.23 (qd, J 11.9, 5.5 1H), 1.20-1.30 (m, 1H), 1.44 (m7, J 6.3, 1H), 1.62 (s, 3H), 1.66-2.05 (m, 5H), 2.25-2.49 (m, 4H), 9.77 (t, J 1.9, 1H) ppm.

$^{13}$C NMR (125 MHz, CDCl$_3$): δ 19.1 (q), 19.7 (q), 19.9 (q), 25.7 (t), 26.7 (t), 30.1 (t), 32.3 (d), 35.7 (d), 40.7 (d), 42.6 (t), 127.6 (s), 127.6 (s), 202.9 (d);

3-(4-isopropyl-6-methylcyclohex-1-en-1-yl)propanal as a mixture of trans and cis isomers (1:3).

Cis Isomer Characteristic Signals $^1$H NMR (500 MHz, CDCl$_3$): δ 1.00 (d, J 7.1, 3H), 5.41 (d, J 5.5, 1H) 9.75 (t, J 1.9, 1H)

$^{13}$C NMR (125 MHz, CDCl$_3$): δ 19.5 (q), 19.8 (q), 19.9 (q), 26.8 (t), 29.4 (t), 32.4 (d), 33.4 (t), 40.2 (d), 42.0 (t), 122.4, 121.5 (d), 140.0, 139.4 (s), 202.9 (d);

Example 2

Synthesis of Compounds of Formula (I); i.e Mixture of 3-(4-isobutyl-2-methylcyclohex-1-en-1-yl) propanal and 3-(4-isobutyl-6-methylcyclohex-1-en-1-yl)propanal a) Preparation of 4-isobutyl-2-methylcyclohexan-1-one
A solution of the 4-isobutyl-2-methylcyclohexan-1-ol (13.4 g, 79 mmol) in dichloromethane (20 mL) was added to a stirred suspension of PCC (22.05 g, 102 mmol) and silica (25 g) in dichloromethane (100 mL) at ambient temperature. After stirring the suspension was diluted with MTBE (50 mL) and then filtered through a plug of silica (5 cm) and the solvents removed in vacuo to yield the crude ketone, 13.3 g. Further purification by bulb to bulb (Kügelrohr) distillation 95-100° C. at 0.5 mbar gave the pure ketone, 11.4 g (86%) as a mixture of cis and trans isomers ratio 1:3
$^1$H NMR (500 MHz, CDCl$_3$) δ 0.89 (d, J 1.9, 3H), 0.91 (d, J 1.6, 3H), 1.00 (d, J 6.4, 3H), 1.02 (m, 1H), 1.12 (t, J 7.2, 2H), 1.24-1.34 (m, 2H), 1.58-1.76 (m, 2H), 1.83-1.98 (m, 2H), 2.02-2.09 (m, 2H), 2.33-2.46 (m, 3H) ppm.
$^{13}$C NMR (125 MHz, CDCl$_3$): δ 14.6 (q), 22.8, 22.8 (q), 25.3 (d), 34.1 (t), 34.5 (d), 41.3 (t), 42.7 (t), 44.4 (d), 45.4 (t), 213.7 (s) ppm. Minor isomer $^{13}$C NMR (125 MHz, CDCl$_3$): δ 16.1 (q), 22.7 (q), 25.6 (d), 29.1 (d), 32.1 (t), 37.6 (t), 39.6 (t), 41.9 (t), 42.8 (t), 215.0 ppm.

b) Preparation of 1-(2-(1,3-dioxolan-2-yl)ethyl)-4-isobutyl-2-methylcyclohexan-1-ol
Under atmosphere of argon, to a suspension of magnesium turnings (2.38 g, 98 mmol) in THF (60 mL), a solution of 2-(2-bromoethyl)-1,3-dioxolane (17.75 g, 98 mmol) in THF (20 mL) was added slowly dropwise. The exotherm was maintained at 40° C. with a cooling bath. After a further 60 mins of stirring at ambient temperature, a solution of the 4-isobutyl-2-methylcyclohexan-1-one (11.0 g, 98 mmol) in THF (20 mL) was added. After a further 4 hours at ambient temperature, the reaction mixture was poured onto a mixture of ice and saturated ammonium chloride solution, extracted with MTBE twice, and the combined organic phase washed with saturated sodium bicarbonate solution then brine, dried over Na$_2$SO$_4$, filtered and the solvents removed in vacuo to yield the crude alcohol, 17.1 g which was used directly in the next step without further purification.

c) Preparation of a Mixture of 2-(2-(4-isobutyl-2-methyl-cyclohex-1-en-1-yl)ethyl)-1,3-dioxolane and 2-(2-(4-isobutyl-6-methylcyclohex-1-en-1-yl)ethyl)-1,3-dioxolane
The 1-(2-(1,3-dioxolan-2-yl)ethyl)-4-isobutyl-2-methylcyclohexan-1-ol (17.1 g, 63.2 mmol) was dissolved in pyridine (100 mL) and the solution cooled at 0° C. POCl$_3$ (14.5 g, 95 mmol) was added slowly dropwise. The solution was slowly warmed to ambient temperature then heated at 50° C. for 18 hours. The mixture was then cooled and poured cautiously into ice, then extracted with MTBE and the organic phase washed cautiously with saturated NaHCO$_3$ solution, then dilute sulfuric acid (5%, 2x), brine, dried over Na$_2$SO$_4$, filtered and the solvents removed in vacuo to yield the crude acetal, 11.9 g. Further purification by bulb to bulb (Kügelrohr) distillation (120° C. at 0. 1 mbar) gave the acetal, 9.8 g (61%).
Major Isomer
$^1$H NMR (500 MHz, CDCl$_3$): δ 4.83 (t, J 4.8, 1H), 3.99-3.93 (m, 2H), 3.88.3.82 (m, 2H), 2.16-1.62 (m, 5H), 1.61 (s, 3H), 1.58-1.50 (m, 3H), 1.09 (t, J 6.9, 2H), 1.15-1.00 (m, 4H), 0.87 (d, J 1.6, 3H), 0.85 (d, J 1.6, 3H) ppm.
$^{13}$C NMR (125 MHz, CDCl$_3$): δ 18.9 (q), 22.8 (q), 23.1 (q), 24.9 (d), 27.5 (t), 29.6 (t), 30.0 (t), 31.7 (d), 32.4 (t), 39.0 (t), 46.3 (t), 64.9 (t), 104.5 (d), 126.2 (s), 128.8 (s) ppm.
Minor Isomer Characteristic Signals
$^1$H NMR (500 MHz, CDCl$_3$): δ 5.40 (d, J 5.4, 1H), 4.87 (t, J 5.1, 1H), 0.98 (d, J 7.0, 3H) ppm.
$^{13}$C NMR (125 MHz, CDCl$_3$): δ 19.7 (q), 22.7 (q), 22.9 (q), 24.8 (d), 28.8 (t), 31.6 (d), 32.3 (t), 32.9 (d), 40.4 (t), 46.6 (t), 64.8 (t), 104.5 (d), 121.3 (d), 140.8 (s) ppm.

d) Preparation of a Mixture of 3-(4-isobutyl-2-methylcyclohex-1-en-1-yl)propanal and 3-(4-isobutyl-6-methylcyclohex-1-en-1-yl)propanal
The dioxolane (9.8 g, 38 mmol) was dissolved in a mixture of acetone (150 mL) water (50 mL) containing concentrated HCl (1.8 mL) and the mixture was heated under reflux for 5 hours then cooled. The solution was diluted with saturated NaHCO$_3$ solution then extracted with MTBE twice, the combined organic phase was washed with brine, then dried over Na$_2$SO$_4$, filtered and the solvents removed in vacuo to yield the crude aldehyde. Further purification by distillation (Kügelrohr, 1.0 mbar, 95-100° C.) gave the crude aldehyde 8.5 g. Further purification by distillation Fischer (20 cm), 0.1 mbar at 55-65° C. gave the pure aldehyde as a mixture of isomers (trans 3-(4-isobutyl-6-methylcyclohex-1-en-1-yl) propanal, cis 3-(4-isobutyl-6-methylcyclohex-1-en-1-yl) propanal and 3-(4-isobutyl-2-methylcyclohex-1-en-1-yl) propanal in a respective ratio of 6:18:76), 5.8 g. (71%).
3-(4-isobutyl-2-methylcyclohex-1-en-1-yl)propanal
$^1$H NMR (500 MHz, CDCl$_3$): δ 0.86 (d, J 1.9, 3H), 0.87 (d, J 1.6, 3H), 1.09 (t, J 6.9, 2H), 1.06-1.15 (m, 1H), 1.51-1.59 (m, 3H), 1.61 (s, 3H), 1.63-1.73 (m, 2H), 1.87-2.06 (m, 3H), 2.28-2.38 (m, 2H), 2.43-2.49 (m, 2H) 9.77 (t, J 1.9, 1H) ppm.
$^{13}$C NMR (125 MHz, CDCl$_3$): δ 19.0 (q), 22.7 (q), 23.1 (q), 24.9 (d), 25.7 (t), 29.4 (t), 29.8 (t), 31.6 (d), 39.0 (t), 42.6 (t), 46.2 (t), 127.3 (s), 127.5 (s), 202.8 (d) ppm.
3-(4-isobutyl-6-methylcyclohex-1-en-1-yl)propanal as a mixture of trans and cis isomers (1:3)
Cis Isomer Characteristic Signals
$^1$H NMR (500 MHz, CDCl$_3$): δ 0.99 (d, J 7.0, 3H), 5.39 (d, J 5.4, 1H) 9.75 (t, J 1.8, 1H) ppm.
$^{13}$C NMR (125 MHz, CDCl$_3$): δ 19.7 (q), 22.7 (q), 23.1 (q), 24.8 (d), 26.8 (t), 31.5 (d), 31.5 (d), 33.1 (t), 40.3 (d), 42.0 (t), 46.5 (t), 122.2, (d), 139.6 (s), 202.8 (d) ppm.

Example 3

Synthesis of Comparative Compound; i.e Mixture of 3-[6-methyl-4-(2-methyl-2-propanyl)-1-cyclohexen-1-yl]propanal and 3-[2-methyl-4-(2-methyl-2-propanyl)-1-cyclohexen-1-yl]propanal a) Preparation of (1RS,2RS,4RS)1-(2-(1,3-dioxolan-2-yl)ethyl)-4-tert-butyl-2-methylcyclohexan-1-ol
Under atmosphere of argon, to a suspension of magnesium turnings (2.38 g, 98 mmol) in THF (60 mL), a solution of 2-(2-bromoethyl)-1,3-dioxolane (17.75 g, 98 mmol) in THF (20 mL) was added slowly dropwise. The exotherm was maintained at 40° C. with a cooling bath. After a further 60 mins of stirring at ambient temperature, a solution of the 4-tert-butyl-2-methylcyclohexan-1-one (prepared as a mixture of cis and trans isomers according to *Bull. Soc. Chim. Fr.* 1965, 2472) (12.5 g, 65.6 mmol) in THF (20 mL) was added. After a further 4 hours at ambient temperature, the reaction mixture was poured onto a mixture of ice and saturated ammonium chloride solution, extracted with MTBE twice, and the combined organic phase washed with saturated sodium bicarbonate solution then brine, dried over $Na_2SO_4$, filtered and the solvents removed in vacuo to yield the crude alcohol, 14.7 g which was used directly in the next step without further purification.

A small portion was dried under high vacuum for analysis.
$^1$H NMR (500 MHz, $CDCl_3$): δ 0.85 (s, 9H), 0.89 (d, J 6.5 3H) 0.95-1.05 (m, 1 H), 1.11 (q, J 12, 1H), 1.29 (q, J 10.5, 1H), 1.34-1.60 (m, 5H), 1.66-1.77 (m, 4H), 3.82-3.88 (m, 2H), 3.93-3.99 (m, 2H), 4.87 (t, J 4.1, 1H) ppm.
$^{13}$C NMR (125 MHz, $CDCl_3$): δ 15.2 (q), 22.4 (t), 27.6 (q), 28.1 (t), 31.6 (t), 32.3 (s), 34.4 (t), 36.6 (t), 39.2 (d), 47.9 (d), 64.9 (t), 71.7 (s), 104.8 (d) ppm.

b) Preparation of (4RS) 2-(2-(4-tert-butyl)-2-methylcyclohex-1-en-1-yl)ethyl)-1,3-dioxolane and (4RS,6RS) 2-(2-(4-tert-butyl)-6-methylcyclohex-1-en-1-yl)ethyl)-1,3-dioxolane The 1-(2-(1,3-dioxolan-2-yl)ethyl)-4-tert-butyl-2-methylcyclohexan-1-ol (13.1 g, 48.1 mmol) was dissolved in pyridine (80 mL) and the solution cooled at 0° C. $POCl_3$ (11.1 g, 72 mmol) was added slowly dropwise. The solution was slowly warmed to ambient temperature then heated at 50° C. for 24 hours. The mixture was then cooled and poured cautiously into ice, then extracted with MTBE and the organic phase washed cautiously with saturated $NaHCO_3$ solution, then dilute sulfuric acid (5%, 2×), brine, dried over $Na_2SO_4$, filtered and the solvents removed in vacuo to yield the crude acetal, 7.6 g as a mixture of isomers (4:1). Further purification by bulb to bulb (Kügelrohr) distillation (120° C. at 0. 1 mbar) gave the acetals as mixture of isomers (4:1), 3.5 g (30%) plus less pure fractions.

Major Isomer
$^1$H NMR (500 MHz, $CDCl_3$): δ 0.86 (s, 9H), 1.00-1.11 (m, 1H), 1.19-1.27 (m, 2H), 1.62 (s, 3H), 1.65-1.80 (m, 1H), 1.85 (dd, J 16.5, 4.6, 1H), 1.94-2.02 (bs, 1H), 2.11 (t, J 8.0, 1H), 2.25-2.48 (m, 4H), 3.83-3.86 (m, 2H), 3.94-3.09 (m, 2H), 4.83 (t, J 4.8, 1H) ppm.
$^{13}$C NMR (125 MHz, $CDCl_3$): δ 19.9 (q), 24.6 (t), 27.2 (q), 27.4 (t), 30.9 (t), 32.1 (s), 32.4 (t), 33.5 (t), 44.7 (d), 64.9 (t), 104.5 (d), 126.7 (s), 128.8 (s) ppm.

Minor Isomer Characteristic Signals
$^1$H NMR (500 MHz, $CDCl_3$): δ 0.85 (s, 9H), 1.00 (d, J 6.9, 3H), 4.86 (t, J 4.8, 1H) ppm.
$^{13}$C NMR (125 MHz, $CDCl_3$): δ 19.8 (q), 24.6 (t), 27.3 (q), 27.6 (t), 28.7 (t), 32.0 (s), 32.3 (t), 33.8 (t), 34.7 (t), 44.2 (d), 64.9 (t), 104.5 (d), 121.7 (d), 140.5 (s) ppm.

c) Preparation of (4RS)-3-(4-tert-butyl)-2-methylcyclohex-1-en-1-yl)propanal and cis/trans (4RS)-3-(4-tert-butyl)-6-methylcyclohex-1-en-1-yl)propanal A solution of the dioxolane from the previous step (2.9 g, 11.5 mmol) in a mixture of acetone (40 mL) and water (15 mL) containing concentrated HCl (0.6 mL) was heated under reflux for 2 hours then cooled. The reaction mixture was diluted with a saturated solution of $NaHCO_3$ and MTBE, the aqueous phase was re extracted with MTBE, the combined organic phase was washed with brine, then dried over anhydrous $Na_2SO_4$, filtered and the solvent removed in vacuo to yield the crude aldehyde, 2.5 g as a pale yellow oil. Further purification by Kügelrohr bulb to bulb distillation (105-110° C. at 2.0 mbar) gave the pure aldehyde as a mixture of isomers (4:1), 1.3 g, 55% plus less pure fractions.

3-[2-methyl-4-(2-methyl-2-propanyl)-1-cyclohexen-1-yl] propanal
$^1$H NMR (500 MHz, $CDCl_3$): δ 0.86 (s, 9H), 1.08 (qd, J 12.0, 5.5, 1H), 1.18-1.26 (m, 1H), 1.62 (s, 3H), 1.69-2.03 (m, 5H), 2.26-2.49 (m, 4H), 9.77 (t, J 1.9, 1H) ppm.
$^{13}$C NMR (125 MHz, $CDCl_3$): δ 19.2 (q), 24.5 (t), 25.6 (t), 27.2 (q), 30.8 (t), 32.1 (s), 33.5 (t), 42.6 (t), 44.6 (d), 127.5 (s), 127.8 (s), 202.9 (d) ppm.

3-[6-methyl-4-(2-methyl-2-propanyl)-1-cyclohexen-1-yl] propanal

Minor Isomer Characteristic Signals.
$^1$H NMR (500 MHz, $CDCl_3$): δ 0.85 (s, 9H), 1.00 (d, J 7.0, 3H), 5.41 (bd, J 5.4, 1H), 9.75 (t, J 1.9, 1H) ppm.
$^{13}$C NMR (125 MHz, $CDCl_3$): δ 19.8 (q), 26.7 (t), 27.3 (t), 32.0 (q), 33.8 (d), 34.6 (t), 42.0 (t), 44.1 (d), 122.7 (d), 139.3 (s), 202.8 (d) ppm.

Example 4

Preparation of a Perfuming Composition a) Floral Perfuming Composition
A perfuming composition, of the floral type, was prepared by admixing the following ingredients:

| Parts by weight | Ingredient |
|---|---|
| 100 | Acropal[1] |
| 40 | C 12 Aldehyde |
| 10 | C 8 Aldehyde |
| 50 | 1%* Cuminic aldehyde |
| 20 | (3,7-Dimethyl-6-octenyloxy)acetaldehyde |
| 20 | 9-Undecenal |
| 1000 | Coranol ®[2] |
| 300 | Hivernal ®[3] |
| 1000 | 3-(4-Isopropylphenyl)-2-methylpropanal |
| 5000 | Florol ®[4] |
| 20 | 10%* (4-methylphenoxy)acetaldehyde |
| 500 | Lilyflore ®[5] |
| 300 | Mayol ®[6] |
| 500 | (4E)-4-methyl-5-(4-methylphenyl)-4-pentenal |
| 500 | 3-(4,4-dimethyl-1-cyclohexen-1-yl)propanal |
| 140 | 1%* Trans Decenal |
| 100 | 7-(2-methyl-2-propanyl)-2H-1,5-benzodioxepin-3(4H)-one |
| 9600 | |

*in dipropyleneglycol
[1]3/4-(4-methyl-3-pentenyl)-3-cyclohexene-1-carbaldehyde; origin: Firmenich SA, Geneva, Switzerland
[2]4-cyclohexyl-2-methyl-2-butanol; origin: Firmenich SA, Geneva, Switzerland
[3]3-(3,3/1,1-dimethyl-5-indanyl)propanal; origin: Firmenich SA, Geneva, Switzerland
[4]tetrahydro-2-isobutyl-4-methyl-4(2H)-pyranol; origin: Firmenich SA, Geneva, Switzerland
[5](2,5-dimethyl-2,3-dihydro-1H-inden-2-yl)methanol; origin: Firmenich SA, Geneva, Switzerland
[6]cis-4-(1methylethyl)-cyclohexanemethanol; origin: Firmenich SA, Geneva, Switzerland b) Herbaceous, Floral Perfuming Composition
A perfume, of the herbaceous, floral lily of the valley type, was prepared by admixing the following ingredients:

| Parts by weight | Ingredient |
|---|---|
| 200 | Hexyl acetate |
| 500 | Isobornyl acetate |
| 100 | Geranyl acetate |
| 100 | Phenylethyl acetate |
| 50 | Styrallyl acetate |
| 400 | Verdyl acetate |
| 500 | Hexylcinnamic aldehyde |
| 100 | 2-Methyl undecanal |
| 50 | Allyl Amyl Glycolate |
| 50 | Methyl anthranilate |
| 40 | Methyl benzoate |
| 250 | Benzylacetone |
| 150 | (1-Methyl-2-phenyl)ethyl butanoate |
| 10 | 7-Isopropyl-2H,4H-1,5-benzodioxepin-3-one |
| 100 | Cetalox ®[1] |

-continued

| Parts by weight | Ingredient |
|---|---|
| 30 | Raspberry ketone |
| 50 | Citronellyl Nitrile |
| 250 | Coumarine |
| 30 | Damascone Alpha |
| 600 | Dihydromyrcenol |
| 40 | Ethylvanilline |
| 100 | Eugenol |
| 300 | Fructalate ®[2] |
| 400 | Gamma Undecalactone |
| 200 | Geraniol |
| 500 | Habanolide ®[3] |
| 400 | Hedione ®[4] |
| 100 | Allyl heptanoate |
| 100 | Ionone Beta |
| 300 | Iralia ®[5] |
| 500 | Iso E ® Super[6] |
| 100 | Lavandin Grosso essential oil |
| 20 | 1-(2,2,3,6-Tetramethyl-cyclohexyl)-3-hexanol[a] |
| 30 | Methyl Phenylethyl Ether |
| 50 | 2-Ethyl methylbutyrate |
| 20 | Methylparacresol |
| 30 | Crystal Moss oil |
| 100 | Muscenone ® Delta[7] |
| 20 | Neobutenone ® Alpha[8] |
| 100 | Nirvanol ®[9] |
| 20 | 10%* cis-2-methyl-4-propyl-1,3-oxathiane[a] |
| 300 | Phenylhexanol |
| 250 | Rosinol |
| 500 | Salicynile ®[10] |
| 500 | Sclareolate ®[11] |
| 200 | Terpineol |
| 50 | 2-Ethyl-4,4-dimethylcyclohexanone[a] |
| 50 | 2,4-Dimethyl-3-cyclohexene-1-carbaldehyde |
| 260 | Undecavertol ®[12] |
| 500 | 2-Tert-butyl-1-cyclohexyl acetate |
| 100 | Yara Yara |
| 9700 | |

*in dipropyleneglycol
[1] dodecahydro-3a,6,6,9a-tetramethyl-naphtho[2,1-b]furan; origin: Firmenich SA, Geneva, Switzerland
[2] diethyl 1,4-cyclohexane dicarboxylate; origin: Firmenich SA, Geneva, Switzerland
[3] pentadecenolide; origin: Firmenich SA, Geneva, Switzerland
[4] methyl dihydrojasmonate; origin: Firmenich SA, Geneva, Switzerland
[5] mixture of methylionones isomers; origin: Firmenich SA, Geneva, Switzerland
[6] 1-(octahydro-2,3,8,8-tetramethyl-2-naphtalenyl)-1-ethanone; origin: International Flavors & Fragrances, USA
[7] 3-methyl-5-cyclopentadecen-1-one; origin: Firmenich SA, Geneva, Switzerland
[8] 1-(5,5-dimethyl-1-cyclohexen-1-yl)-4-penten-1-one; origin: Firmenich SA, Geneva, Switzerland
[9] 3,3-dimethyl-5-(2,2,3-trimethyl-3-cyclopenten-1-yl)-4-penten-2-ol; origin: Firmenich SA, Geneva, Switzerland
[10] (2Z)-2-phenyl-2-hexenenitrile; origin: Firmenich SA, Geneva, Switzerland
[11] propyl (S)-2-(1,1-dimethylpropoxy)propanoate; origin: Firmenich SA, Geneva, Switzerland
[12] 4-methyl-3-decen-5-ol; origin: Givaudan-Roure SA, Vernier, Suisse By the addition of 400 parts by weight of a mixture obtained in example 1 to the perfuming composition of example 3 a) or the addition of 300° parts by weight of a mixture obtained in example 1 to the perfuming composition of example 3 b), the compositions become more floral and green with a petallic and hyacinth connotation, also perceptible on the bottom note.

When instead of the invention's compound, the same amount of 3-((S)-4-isopropylcyclohex-1-en-1-yl)-2-methylpropanal was used, the composition acquired an aquatic note with a fruity connotation in the direction of melon with a morning dew side, also perceptible on the bottom note.

When instead of the invention's compound, the same amount of (+)-3-[(4R)-4-isopropyl-1-cyclohexen-1-yl]propanal reported in US 2013/0090390, was used, the results was totally different as the composition acquired a green, metallic and citrus note with low impact on the bottom note.

When instead of the invention's compound, the same amount of 3-[(5S)-5-isopropyl-2-methyl-1-cyclohexen-1-yl] propanal was used, the composition acquired an aldehydic, fatty and green/vegetal note with nearly no impact on the bottom note.

The invention claimed is:

1. A compound of formula $$(I)$$

in the form of any one of its stereoisomers or a mixture thereof, and wherein n is 0 or 1; R and R', independently from each other, represent a hydrogen atom or a $C_{1-2}$ linear alkyl group provided that one of said groups represents a hydrogen atom and the other a $C_{1-2}$ linear alkyl group; each $R^1$, independently from each other, represents a hydrogen atom or a methyl group; and $R^2$ and $R^3$ represent, independently of each other, a $C_{1-3}$ linear alkyl group; or $R^2$ and $R^3$, when taken together, represent a $C_{4-5}$ linear or branched alkanediyl or alkenediyl.

2. The compound according to claim 1, characterized in that n is 0.

3. The compound according to claim 1, characterized in that $R^1$ is hydrogen atom.

4. The compound according to claim 1, characterized in that the compound is of formula $$(III)$$

in the form of any one of its stereoisomers or a mixture thereof and wherein; R and R', independently from each other, represent a hydrogen atom or a $C_{1-2}$ linear alkyl group provided that one of said groups represents a hydrogen atom and the other a $C_{1-2}$ linear alkyl group; and $R^2$ and $R^3$ represent, independently of each other, a $C_{1-3}$ linear alkyl group; or $R^2$ and $R^3$, when taken together, represent a $C_{4-5}$ linear or branched alkanediyl or alkenediyl.

5. The compound according to claim 1, characterized in that $R^2$ is a methyl group.

6. The compound according to claim 1, characterized in that $R^3$ is a methyl group.

7. The compound according to claim 1, characterized in that $R^2$ and $R^3$, when taken together, are a $C_4$ linear alkanediyl.

8. The compound according to claim 1, characterized in that R and R', independently from each other, represent a hydrogen atom or a methyl group provided that one of said groups represents a hydrogen atom and the other a methyl group.

9. The compound according to claim 1, characterized in that the compound of formula (I) is a mixture comprising 3-(4-isopropyl-6-methyl-1-cyclohexen-1-yl)propanal and 3-(4-isopropyl-2-methyl-1-cyclohexen-1-yl)propanal.

10. A method to confer, enhance, improve or modify the odor properties of a perfuming composition or of a perfumed article, which method comprises adding to said composition or article an effective amount of at least one compound of formula (I) as defined in claim 1.

11. A method of using a compound of formula (I) as defined in claim 1, the method comprising using the compound of formula (I) as a perfuming ingredient.

12. A perfuming composition comprising:
i) at least one compound of formula (I), as defined in claim 1;
ii) at least one ingredient selected from the group consisting of a perfumery carrier and a perfumery base; and
iii) optionally at least one perfumery adjuvant.

13. A perfumed consumer product comprising at least one compound of formula (I), as defined in claim 1.

14. The perfumed consumer product according to claim 13, characterized in that the product is a perfume, a fabric care product, a body-care product, a cosmetic preparation, a skin-care product, an air care product or a home care product.

15. The perfumed consumer product according to claim 14, characterized in that the perfumery consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product or a car care product.

16. A perfumed consumer product comprising the composition as defined in claim 12.

17. The compound according to claim 9, characterized in that the compound of formula (I) is the mixture comprising 3-(4-isopropyl-6-methyl-1-cyclohexen-1-yl)propanal and 3-(4-isopropyl-2-methyl-1-cyclohexen-1-yl)propanal in a respective molar ratio of 25:75.

* * * * *